(12) United States Patent
Graf et al.

(10) Patent No.: US 9,259,307 B2
(45) Date of Patent: *Feb. 16, 2016

(54) TISSUE REPAIR ASSEMBLY

(71) Applicant: Smith & Nephew, Inc., Memphis, TN (US)

(72) Inventors: Ben Kim Graf, Madison, WI (US); Paul Alexander Torrie, Marblehead, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/336,239

(22) Filed: Jul. 21, 2014

(65) Prior Publication Data

US 2014/0330381 A1 Nov. 6, 2014

Related U.S. Application Data

(63) Continuation of application No. 12/791,043, filed on Jun. 1, 2010, now Pat. No. 8,858,606, which is a continuation-in-part of application No. 12/631,960, filed on Dec. 7, 2009, now Pat. No. 8,529,610.

(60) Provisional application No. 61/120,898, filed on Dec. 9, 2008.

(51) Int. Cl.
*A61F 2/08* (2006.01)
*A61B 17/04* (2006.01)

(52) U.S. Cl.
CPC .......... *A61F 2/0811* (2013.01); *A61B 17/0401* (2013.01); *A61B 17/0485* (2013.01); *A61B 2017/0446* (2013.01); *A61B 2017/0448* (2013.01); *A61B 2017/0458* (2013.01); *A61F 2002/0829* (2013.01); *A61F 2002/0841* (2013.01); *A61F 2002/0852* (2013.01); *A61F 2002/0864* (2013.01); *A61F 2002/0882* (2013.01); *A61F 2002/0888* (2013.01)

(58) Field of Classification Search
CPC ... A61F 2/0805; A61F 2/0811; A61F 2/0858; A61B 17/8645
See application file for complete search history.

(56) References Cited

U.S. PATENT DOCUMENTS

| 2,381,050 A | 8/1945 | Hardinge |
|---|---|---|
| 4,462,395 A | 7/1984 | Johnson |

(Continued)

FOREIGN PATENT DOCUMENTS

| FR | 2622430 | 10/1987 |
|---|---|---|
| JP | H05-184521 | 7/1993 |

(Continued)

OTHER PUBLICATIONS

Office action received in corresponding Chinese application No. 200980156772.1 mailed Jul. 25, 2014.

(Continued)

*Primary Examiner* — Andrew Yang
(74) *Attorney, Agent, or Firm* — Norman F. Hainer, Jr.

(57) ABSTRACT

The present disclosure relates to a fixation device. The fixation device includes a base portion including a first leg, a second leg, and a groove located between the first and second legs and a top portion extending from the base portion. A tissue repair device and a method of tissue repair are also disclosed.

9 Claims, 17 Drawing Sheets

(56) References Cited

U.S. PATENT DOCUMENTS

| | | |
|---|---|---|
| 5,098,435 A | 3/1992 | Stednitz et al. |
| 5,324,308 A | 6/1994 | Pierce |
| 5,486,197 A | 1/1996 | Le et al. |
| 5,643,264 A | 7/1997 | Sherman et al. |
| 5,713,903 A | 2/1998 | Sander et al. |
| 5,766,250 A | 6/1998 | Chervitz et al. |
| 5,782,865 A | 7/1998 | Grotz |
| 5,840,078 A | 11/1998 | Yerys |
| 6,524,317 B1 | 2/2003 | Ritchart et al. |
| 6,616,665 B2 | 9/2003 | Grafton et al. |
| 6,916,321 B2 | 7/2005 | TenHuisen et al. |
| 6,984,241 B2 | 1/2006 | Lubbers et al. |
| 7,517,357 B2 | 4/2009 | Abrams et al. |
| 7,572,283 B1* | 8/2009 | Meridew ............... 606/321 |
| 2001/0051807 A1 | 12/2001 | Grafton |
| 2002/0007182 A1 | 1/2002 | Kim |
| 2002/0147463 A1 | 10/2002 | Martinek |
| 2003/0153921 A1 | 8/2003 | Stewart et al. |
| 2004/0176768 A1* | 9/2004 | Singhatat ............... 606/72 |
| 2005/0080455 A1 | 4/2005 | Schmieding et al. |
| 2005/0177157 A1 | 8/2005 | Jahng |
| 2005/0277923 A1 | 12/2005 | Sweeney |
| 2006/0004364 A1 | 1/2006 | Green et al. |
| 2006/0100630 A1 | 5/2006 | West, Jr. |
| 2006/0189993 A1 | 8/2006 | Stone |
| 2006/0217713 A1 | 9/2006 | Serhan et al. |
| 2006/0271060 A1 | 11/2006 | Gordon |
| 2007/0225719 A1 | 9/2007 | Stone et al. |
| 2009/0287259 A1 | 11/2009 | Trenhaile et al. |

FOREIGN PATENT DOCUMENTS

| | | |
|---|---|---|
| JP | H08-066410 | 12/1996 |
| JP | 2000-229087 | 8/2000 |
| WO | 2007002829 | 1/2007 |
| WO | 2007025279 | 3/2007 |
| WO | 2008005427 | 1/2008 |

OTHER PUBLICATIONS

Office action received in corresponding Australian patent application No. 20093333625 mailed Nov. 21, 2014.

Office action received in corresponding Japanese application No. 2011-540798 mailed Feb. 16, 2015.

Office action received in corresponding European application No. 09 793 374.1-1654 mailed Mar. 12, 2015.

* cited by examiner

TISSUE REPAIR ASSEMBLY

CROSS-REFERENCE TO RELATED APPLICATIONS

This application is a continuation application claiming priority to pending U.S. application Ser. No. 12/791,043 filed Jun. 1, 2010, which is a Continuation-In-Part of granted U.S. Pat. No. 8,529,610 issued Sep. 10, 2013, which claimed benefit of U.S. Provisional Application No. 61/120,898 filed Dec. 9, 2008, all of which are incorporated by reference herein in their entireties.

BACKGROUND

1. Field of Technology

The present disclosure relates generally to soft tissue repair, and more specifically, devices and methods used for such repair.

2. Related Art

Current devices available for arthroscopic soft tissue repair include suture anchors, metal post and washer screws, and interference screws. These devices provide immediate fixation of the tissue to the bone with little postoperative activity modification. However, the tissue must be delivered out of the body, stitched, and then re-inserted into a previously drilled bone hole. This reinsertion can be done through a portal, but is very technically demanding, precluding some patients from being a candidate for this procedure. Additionally, these devices don't prevent the tissue from sliding past the device as the device is inserted into the bone hole and/or when repetitive loads are applied to the soft tissue after fixation. Slippage of the tissue past the device may lead to decreased or failed fixation of the tissue to the bone and therefore an unsuccessful repair.

Therefore, a procedure is needed that is simple, reproducible, and that would allow both beginner and experienced surgeons to perform the procedure. Similarly, the devices used in the procedure would be simple to use, cost effective, and marketable to arthroscopic and open surgery surgeons alike and configured to prevent the tissue from sliding past the devices.

SUMMARY

In one aspect, the present disclosure relates to a fixation device. The fixation device includes a base portion including a first leg, a second leg, and a groove located between the first and second legs; and a top portion extending from the base portion. In an embodiment, the first leg of the device includes a through hole. In another embodiment, the top portion includes a first side and a second side, the first side including a plurality of bone engaging elements. In yet another embodiment, the groove is U-shaped.

In another aspect, the present disclosure relates to a tissue repair assembly. The assembly includes a fixation device including a base portion having a first leg, a second leg, and a groove located between the first and second legs, and a top portion extending from the base portion; and an interference device coupled to the fixation device. In an embodiment, the interference device is cannulated. In another embodiment, the interference device is coupled to the first leg of the fixation device. In yet another embodiment, the interference device includes threads on an outer surface of the interference device. In a further embodiment, the interference device is configured for rotary advancement into a target tissue.

In yet another aspect, the present disclosure relates to a method of tissue repair. The method includes preparing a hole in a bone; and fixating a soft tissue into the hole via the use of a tissue repair assembly. In an embodiment, the tissue repair assembly comprises a fixation device and an interference device coupled to the fixation device. In another embodiment, the step of fixating a soft tissue into the hole further includes inserting the soft tissue into the hole and inserting the tissue repair assembly into the hole to fixate the soft tissue within the hole. In yet another embodiment, the step of fixating a soft tissue into the hole further includes inserting the soft tissue and the tissue repair assembly into the hole together. In a further embodiment, the fixation device includes a base portion having a first leg, a second leg, and a groove located between the legs, and a top portion extending from the base portion.

In yet a further embodiment, the soft tissue is located within the groove of the fixation device when the soft tissue is advanced into the hole. In an embodiment, inserting the interference device into the hole fixates the soft tissue to the bone. In another embodiment, the fixation device includes bone engaging elements. In yet another embodiment, the interference device applies compression to the fixation device such that the bone engaging elements engage the bone. In a further embodiment, the interference device includes threads on an outer surface of the fixation device. In yet a further embodiment, the threads allow for compression of the graft against a wall of the bone tunnel.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION OF THE EMBODIMENTS

The following description of the preferred embodiment(s) is merely exemplary in nature and is in no way intended to limit the disclosure, its application, or uses.

Figure 1:
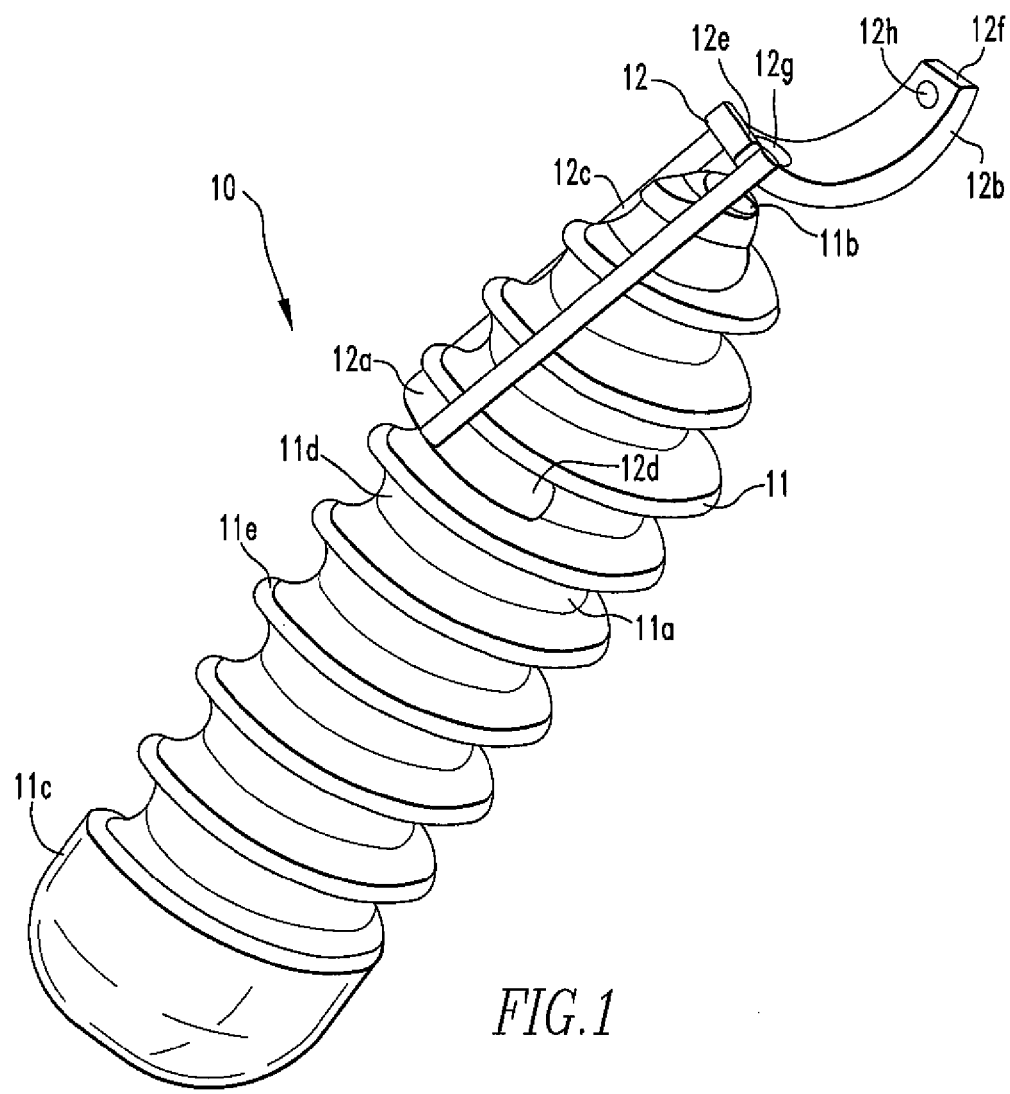
FIG. 1 shows a perspective view of a first tissue repair assembly of the present disclosure.

FIG. 1 shows a first tissue repair assembly 10 of the present disclosure. The assembly 10 includes an interference device 11 having a tapered body 11a and a cannulation 11b. The body 11a includes a first portion 11e and a second portion 11d having threads 11e. The assembly 10 also includes a fixation device 12 coupled to the interference device 11. The fixation device 12 includes a coupling portion 12a and a capturing portion 12b. The coupling portion 12a includes a shaft 12c and a coupler 12d. The coupler 12d includes an open-ended shape, such as a semi-circular shape, and is configured to provide a snap-fit connection to the body 11a of the interference device 11. The capturing portion 12b also includes a semi-circular shape and has a first end 12e and a second end 12f. The first end 12e includes a first opening 12g and the second end 12f includes a second opening 12h. The first opening 12g is aligned with the cannulation and is configured to house a guide wire, as will be further discussed below, and the second opening 12h is configured to house a suture, as will be further described below.

Figure 2:
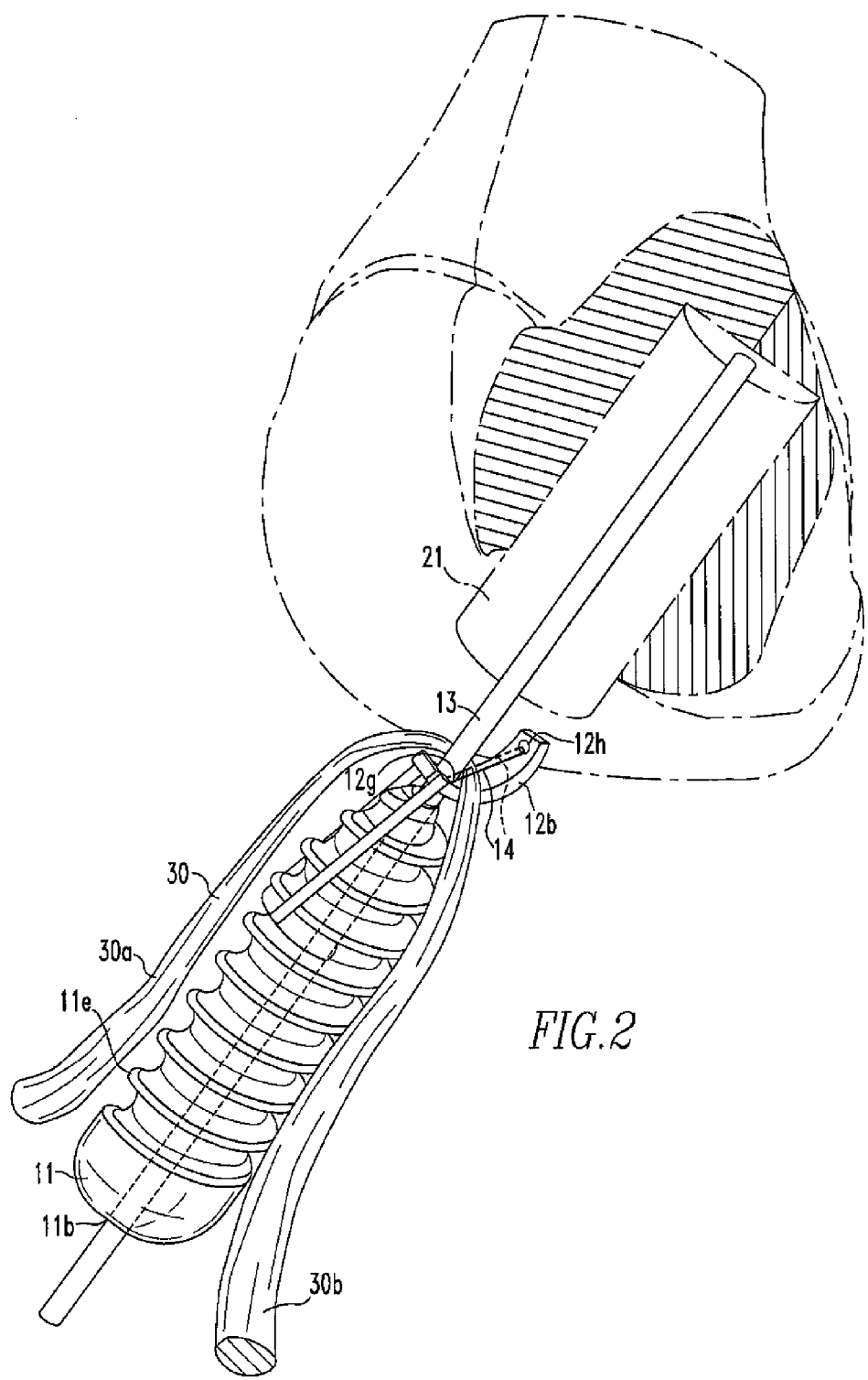
FIG. 2 shows a perspective view of the tissue repair assembly of FIG. 1 during soft tissue repair.

FIG. 2 shows the assembly 10 disposed on a guide wire 13. The guide wire 13 is advanced into a bone tunnel 21, such as a tibial tunnel of a knee joint, and the assembly 10 is disposed on the guide wire 13, such that the guide wire 13 is passed through the first opening 12g and the cannulation 11b. A soft tissue graft 30 rests on the capturing portion 12b with each end 30a,30b of the graft 30 draped over the interference device 11. A suture 14 may be used to further capture the graft 30 on the capturing portion 12b by placing ends of the suture 14 through openings 12g,12h, such that the suture 14 is placed over the tissue 30, and then tying the ends of the suture 14. The assembly 10 and graft 30 are advanced into the bone tunnel 21, via a delivery device (not shown). The threads 11e allow for compression of the graft 30 against the walls of the bone tunnel 21.

Figure 3:
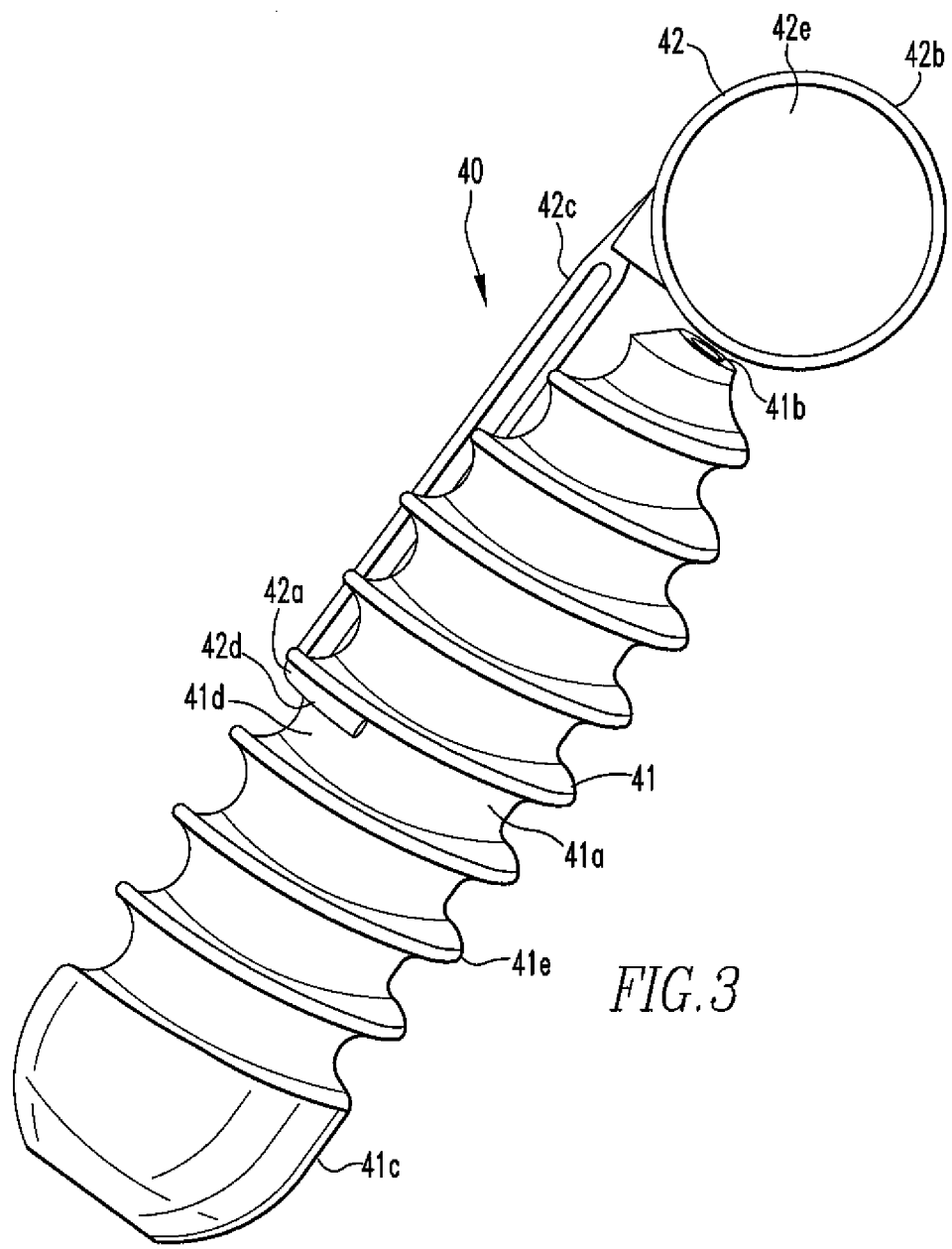
FIG. 3 shows a perspective view of a second tissue repair assembly of the present disclosure.

FIG. 3 shows a second tissue repair assembly 40 of the present disclosure. The assembly 40 includes an interference device 41 having a tapered body 41a and a cannulation 41b. The body 41a includes a first portion 41c and a second portion 41d having threads 41e. The assembly 40 also includes a fixation device 42 coupled to the interference device 41. The fixation device 42 includes a coupling portion 42a and a capturing portion 42b. The coupling portion 42a includes a shaft 42c and a coupler 42d. The coupler 42d includes a semi-circular shape and is configured to provide a snap-fit connection to the body 41a of the interference device 41. The capturing portion 42b is in a closed-ended shape, such as a loop, and includes a through hole 42e configured for disposal of a soft tissue graft.

Figure 4:
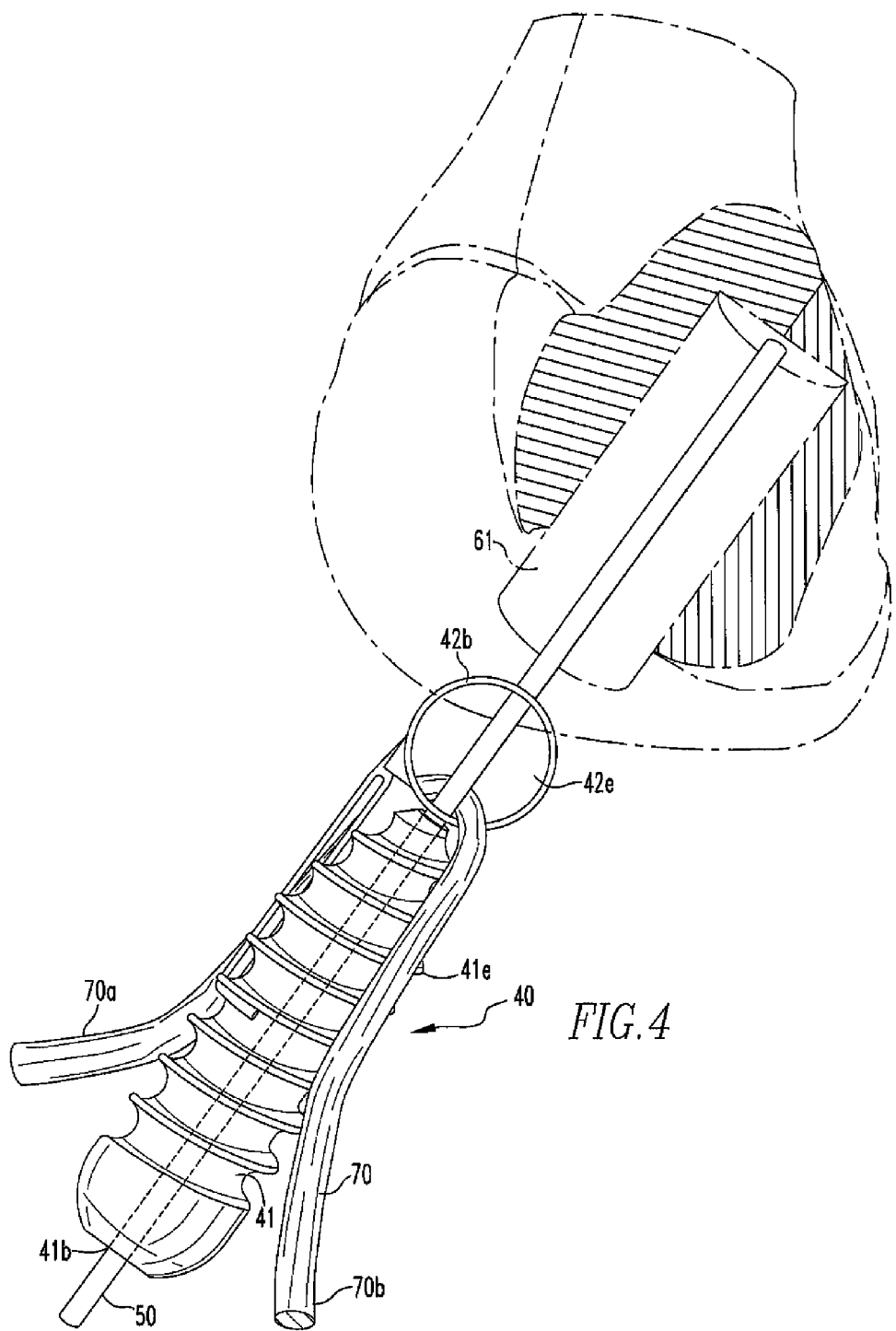
FIG. 4 shows a perspective view of the tissue repair assembly of FIG. 3 during soft tissue repair.

FIG. 4 shows the assembly 40 located on a guide wire 50. The guide wire 50 is advanced into a bone tunnel 61, such as a tibial tunnel of a knee joint, and the assembly 40 is disposed on the guide wire 50, such that the guide wire 50 is passed through the cannulation 41b. A soft tissue graft 70 is disposed through the hole 42e of the caturing portion 42b with each end 70a,70b of the graft 70 draped over the interference device 41. The assembly 40 and graft 70 are advanced into the bone tunnel 61, via a delivery device (not shown). The threads 41e allow for compression of the graft 70 against the walls of the bone tunnel 61.

Figure 5:
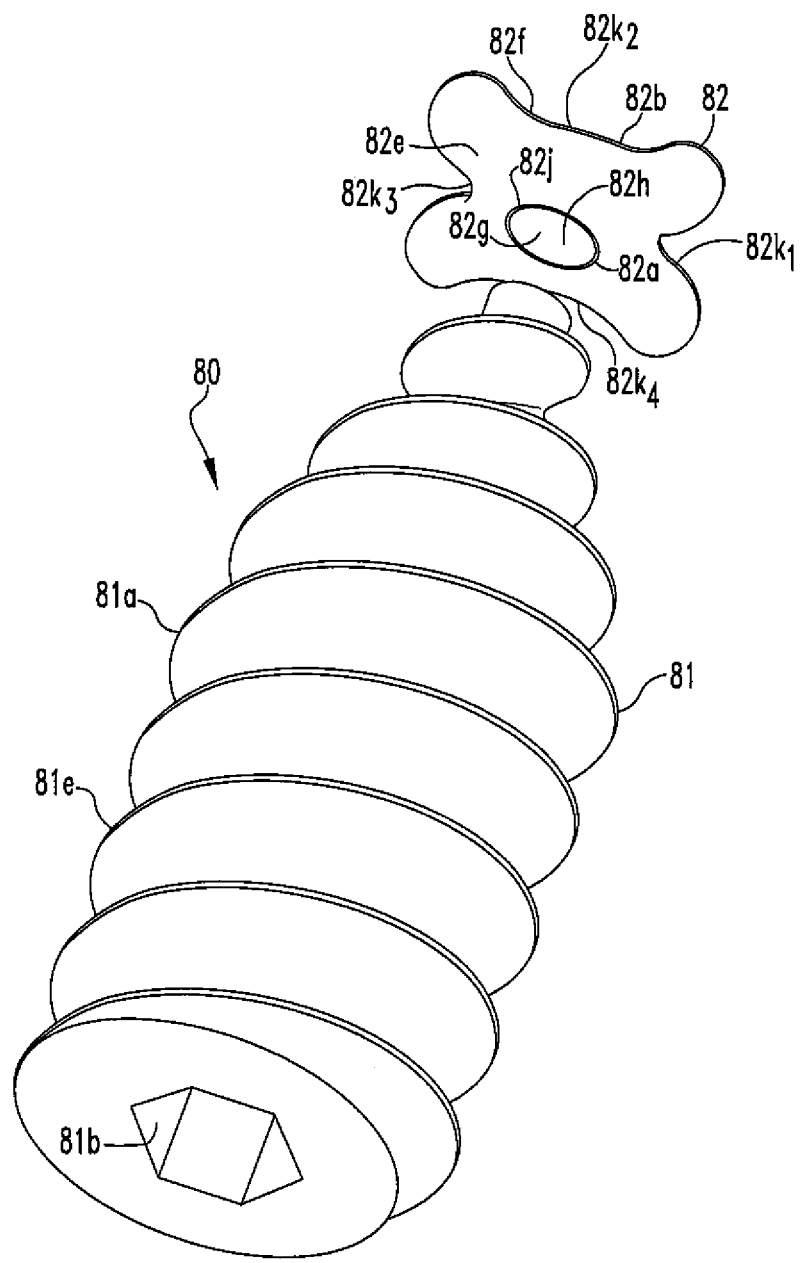
FIG. 5 shows a perspective view a third tissue repair assembly of the present disclosure.

FIG. 5 shows a third tissue repair assembly 80 of the present disclosure. The assembly 80 includes an interference device 81 having a tapered body 81a having threads 81e and a cannulation 81b. The assembly 80 also includes a fixation device 82 coupled to the interference device 81. The fixation device 82 includes a coupling portion 82a and a capturing portion 82b. The capturing portion 82b includes a top surface 82e, a bottom surface 82f, and a through hole 82g. The through hole 82g includes a first opening 82h located on the top surface 82e and a second opening (not shown) located on the bottom surface 82f. A rim 82j surrounds the first opening 82h and serves as the coupling portion 82a to couple the fixation device 82 to the interference device 81. The rim 82j includes a diameter equal to an inner diameter of the interference device 81. For the purposes of this disclosure, the capturing portion 82b includes four grooves $82k_1$-$82k_4$. However, the capturing portion 82b may have less than four grooves, such as the two grooves $82k_1$,$82k_3$ for housing of end portions of a soft tissue graft, as will be further described below. In addition, it is also within the scope of this disclosure for the rim 82j to have a diameter less than or greater than an inner diameter of the interference device 81.

Figure 6:
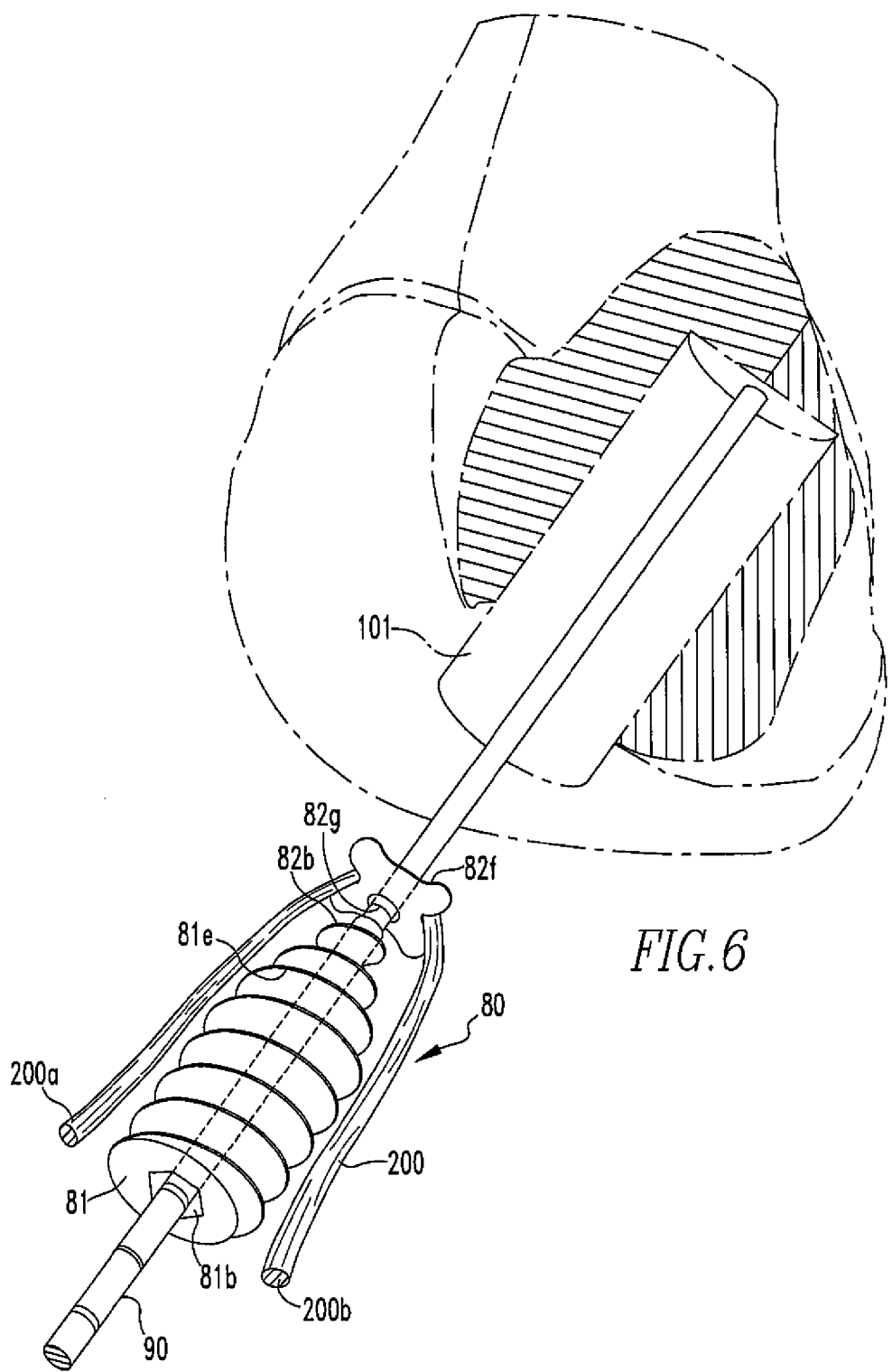
FIG. 6 shows a perspective view of the tissue repair assembly of FIG. 5 during soft tissue repair.

FIG. 6 shows the assembly 80 located on a guide wire 90. The guide wire 90 is advanced into a bone tunnel 101, such as a tibial tunnel of a knee joint, and the assembly 80 is disposed on the guide wire 90, such that the guide wire 90 is passed through the cannulation 81b and the through hole 82g of the capturing portion 82b. A soft tissue graft 200 rests on the bottom surface 82f of the capturing portion 82b with each end 200a,200b of the graft 200 draped over the interference device 81 and housed in grooves $82k_1$, $82k_3$. The assembly 80 and graft 200 are advanced into the bone tunnel 101, via a delivery device (not shown). The threads 81e allow for compression of the graft 200 against the walls of the bone tunnel 101.

For the purposes of FIGS. 5 and 6, it is within the scope of this disclosure for the capturing portion to not have grooves. Rather the sides of the capturing portion may be straight such that the portion is in the shape of a square. Other shapes are also within the scope of this disclosure.

Figure 7:
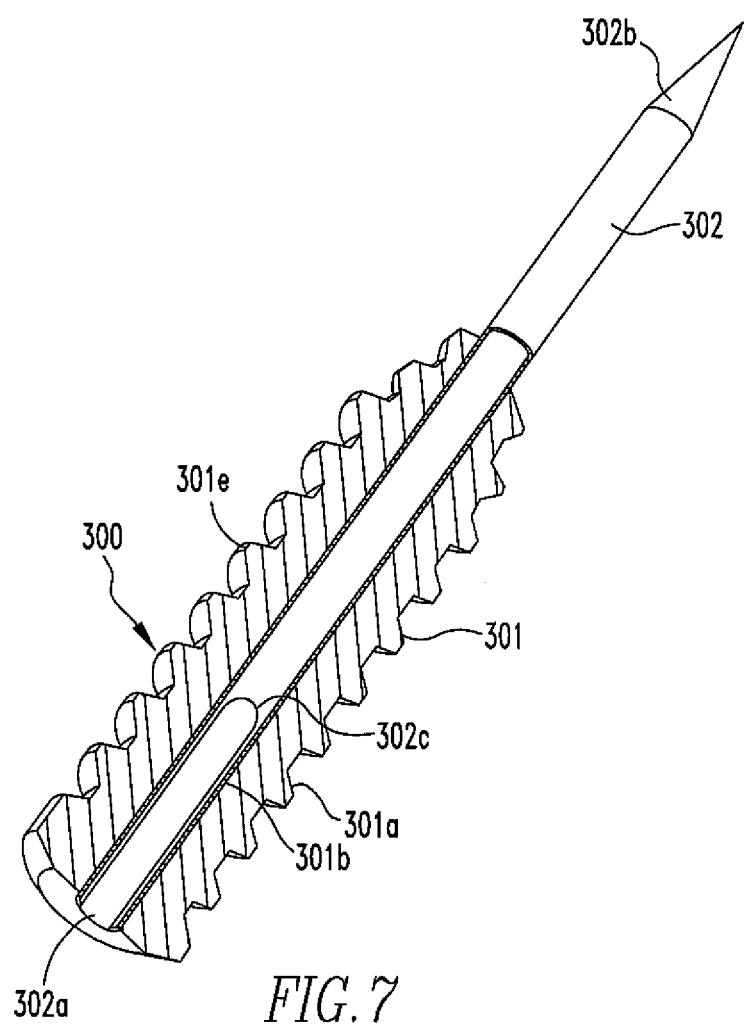
FIG. 7 shows a cross-sectional view of a fourth tissue repair assembly of the present disclosure.

FIG. 7 shows a fourth tissue repair assembly 300 of the present disclosure. The assembly 300 includes an interference device 301 having a tapered body 301a with threads 301e and a cannulation 301b. The assembly 300 also includes a fixation device 302 disposed within the cannulation 301b of the interference device 301. The fixation device 302 includes a proximal end 302a, a pointed distal end 302b, and a channel 302c extending a partial length of the fixation device 302.

Figure 8:
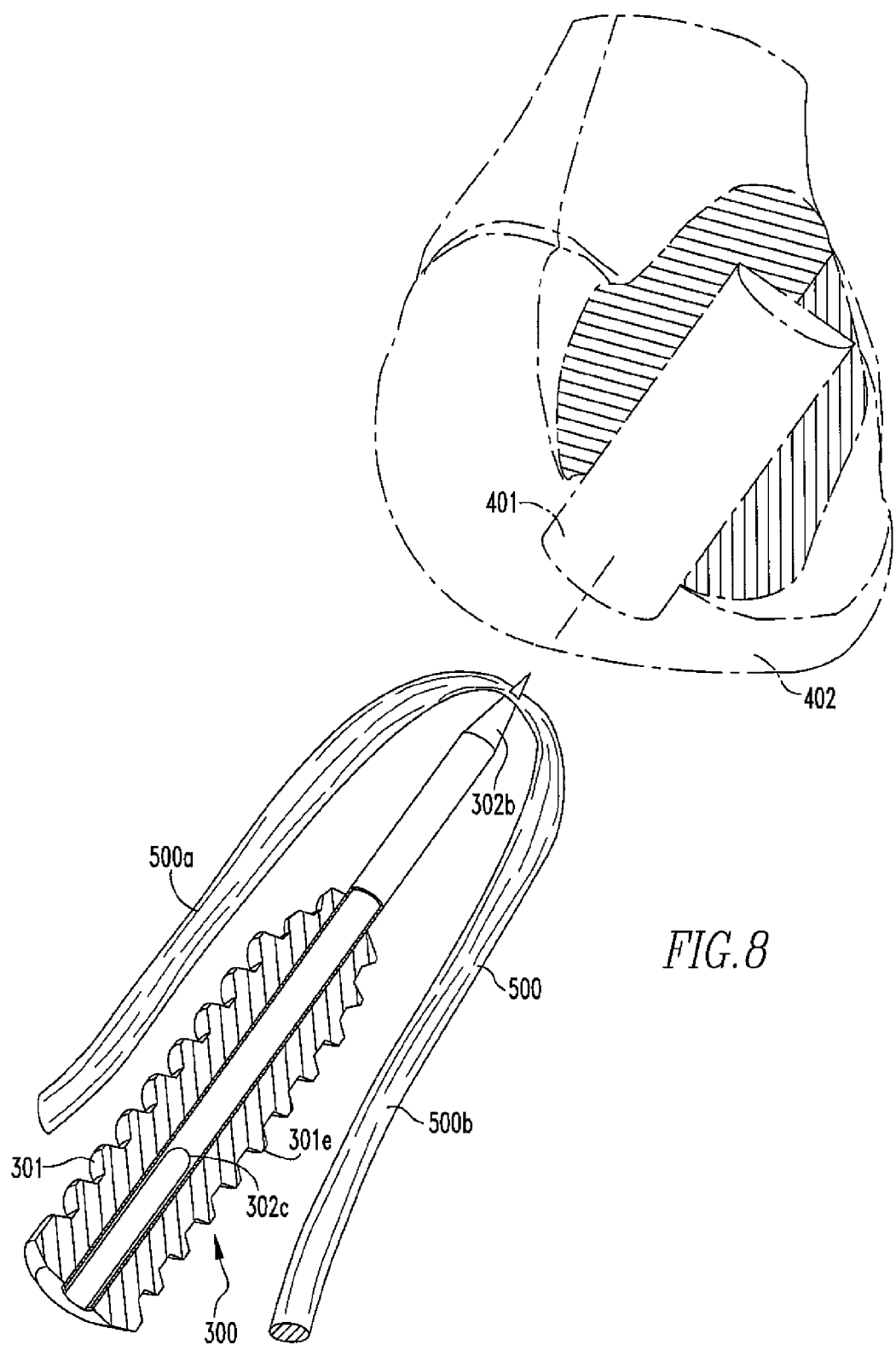
FIG. 8 shows a perspective view of the tissue repair assembly of FIG. 7 during soft tissue repair.

FIG. 8 shows the assembly 300 being advanced into a bone tunnel 401, such as a tibial tunnel of a knee joint. A delivery device (not shown) is inserted into the channel 302c and the delivery device (not shown) is used to insert a soft tissue graft 500 into the bone tunnel 401. The soft tissue graft 500 rests on the pointed distal end 302b with each end 500a,500b of the graft 500 draped over the interference device 301. The assembly 300 and graft 500 are advanced into the bone tunnel 401, via the delivery device (not shown) and the pointed distal end 302b extends through the graft 500 and into bone 402. The threads 301e allow for compression of the graft 500 against the walls of the bone tunnel 401.

Alternatively, the graft 500 is inserted into the tunnel 401, the fixation device 302 is inserted into the tunnel 401 such that the pointed distal end 302b engages the graft, possibly being inserted through the graft 500 and into the bone 402, and then the interference device 301 is inserted into the tunnel 401 such that the fixation device 302 is housed within the cannulation 301b and the ends 500a,500b of the graft 500 are draped over the device 301. Insertion of the interference device 301 into the tunnel 401 directly after inserting the tissue 500 into the tunnel 401 and subsequently inserting the fixation device 302 into the cannulation 301b such that the pointed end 302b is inserted through the graft 500 and possibly into the bone 402, is also within the scope of the disclosure. The fixation device 302 may be of a variety of lengths and may include surface features that mate with surface features located within the cannulation 301b to further couple the fixation device 302 to the interference device 301. The surface features may include threads, barbs, ribs, or other surface features known to one of skill in the art and that have the ability to further facilitate coupling between the fixation device 302 and the interference device 301. It is also within the scope of this disclosure for the fixation device 302 and/or the interference device 301 to be made out of a material, such as a shape memory material, that expands or otherwise allows for further coupling between the devices 301,302 in response to body temperature or an external energy source.

Figures 9A, 9B:
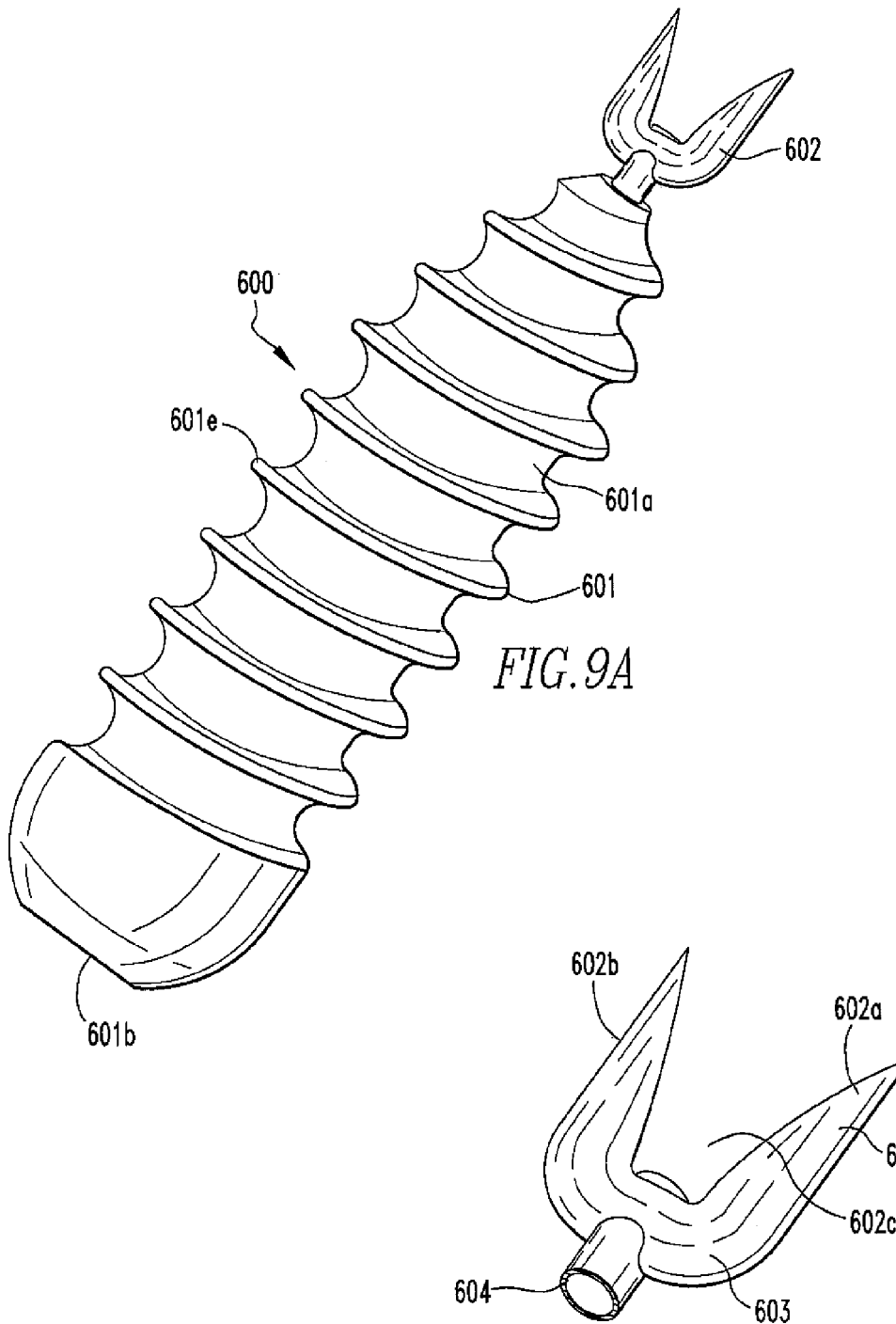
FIG. 9A shows a perspective view a fifth tissue repair assembly of the present disclosure.
FIG. 9B shows a perspective view of the fixation device of the tissue repair assembly of FIG. 9A.

FIG. 9A shows a fifth tissue repair assembly 600 of the present disclosure. The assembly 600 includes an interference device 601 having a tapered body 601a with threads 601e and a cannulation 601b. The assembly 600 also includes a fixation device 602 disposed within the cannulation 601b of the interference device 601. As shown in FIG. 9B, the fixation device 602 includes a first leg 602a, a second leg 602b, and a groove 602c located between the legs 602a,602b. The device 602 also includes a top portion 604 extending from the base portion 603. As can be seen in FIG. 9A, the top portion 604 has a smaller diameter than the cannulation 601b so as to allow the top portion 604 to be disposed within the cannulation 601b. In addition, the device 602 is cannulated to allow passage of a guide wire 610 through both the interference device 601 and the fixation device 602. As will be further described below, the legs 602a,602b and the groove 602c cooperate to house soft tissue within the groove and fixate the tissue within a bone tunnel. For the purposes of FIGS. 9A and 9B, the fixation device 902 is U-shaped. However, the device may be V-shaped or have any other shape known to one of skill in the art.

Figure 10:
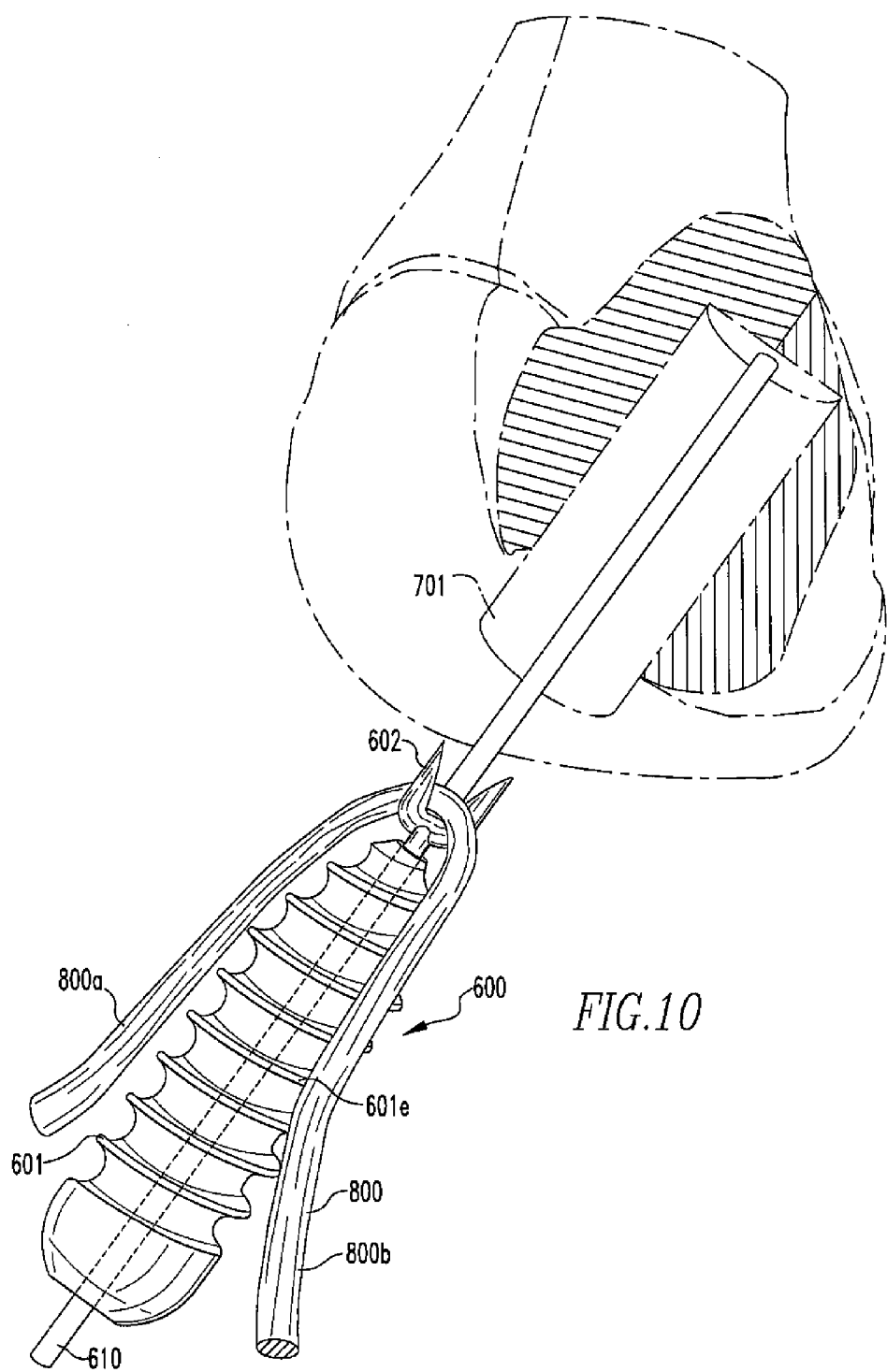
FIG. 10 shows a perspective view of the tissue repair assembly of 9A during soft tissue repair.

FIG. 10 shows the assembly 600 located on the guide wire 610. The guide wire 610 is advanced into a bone tunnel 701, such as a tibial tunnel of a knee joint, and the assembly 600 is disposed on the guide wire 610, such that the guide wire 610 is passed through both the interference device 601 and the fixation device 602. A soft tissue graft 800 rests between the legs 602a,602b with each end 800a,800b of the graft 800 draped over the interference device 601. The assembly 600 and graft 800 are advanced into the bone tunnel 701 together, via a delivery device (not shown). The threads 601e allow for compression of the graft 800 against the walls of the bone tunnel 701. Alternatively, the assembly 600 may be advanced into the tunnel 701 such that the fixation device 602 is advanced into the tunnel 701 followed by advancement of the interference device 601. In this manner, tension may be applied to the soft tissue 800 prior to inserting the interference device 601 into the tunnel 701.

Figure 11:
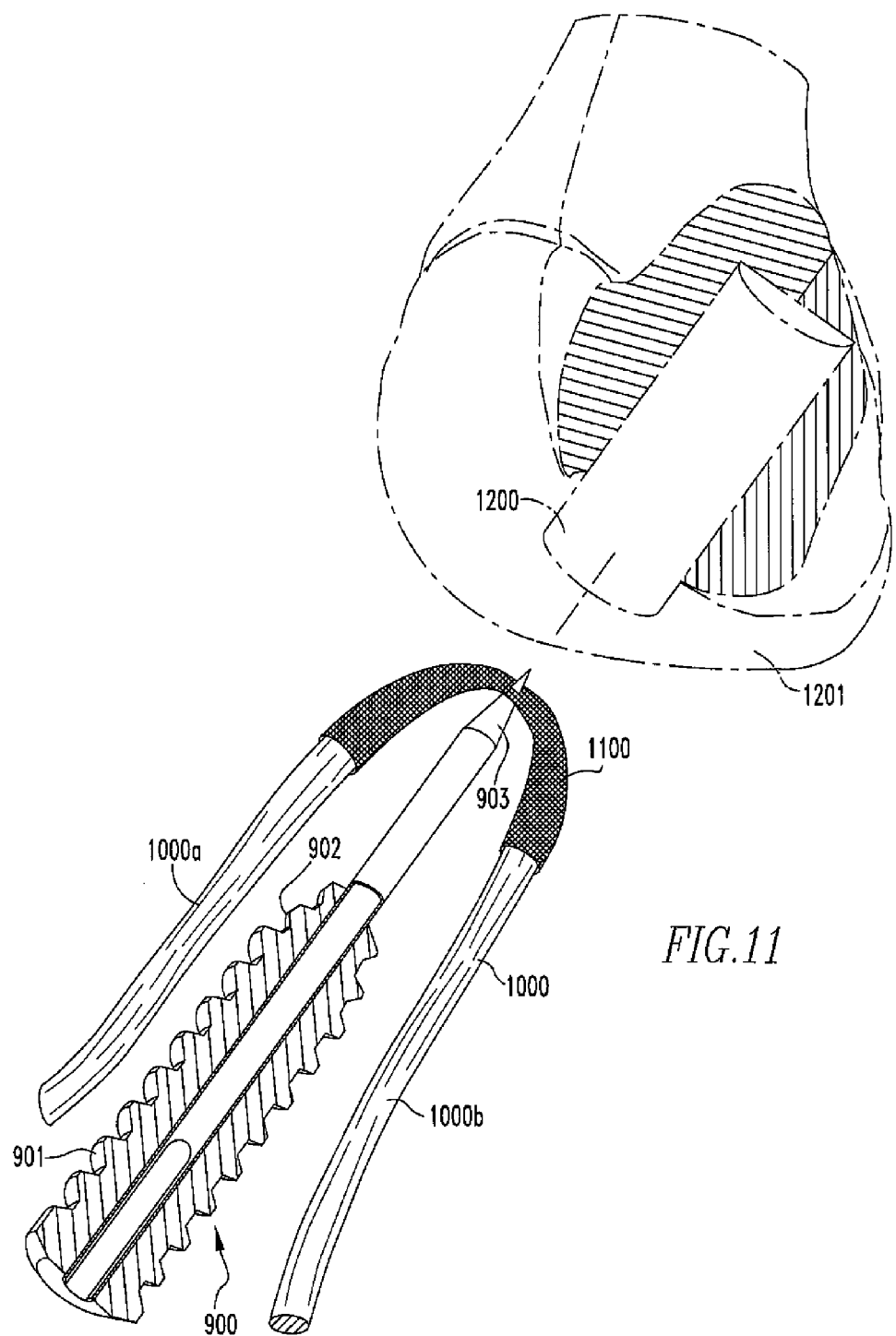
FIG. 11 shows a perspective view of the fourth tissue repair assembly during soft tissue repair wherein the soft tissue includes a sleeve.
Figure 12:
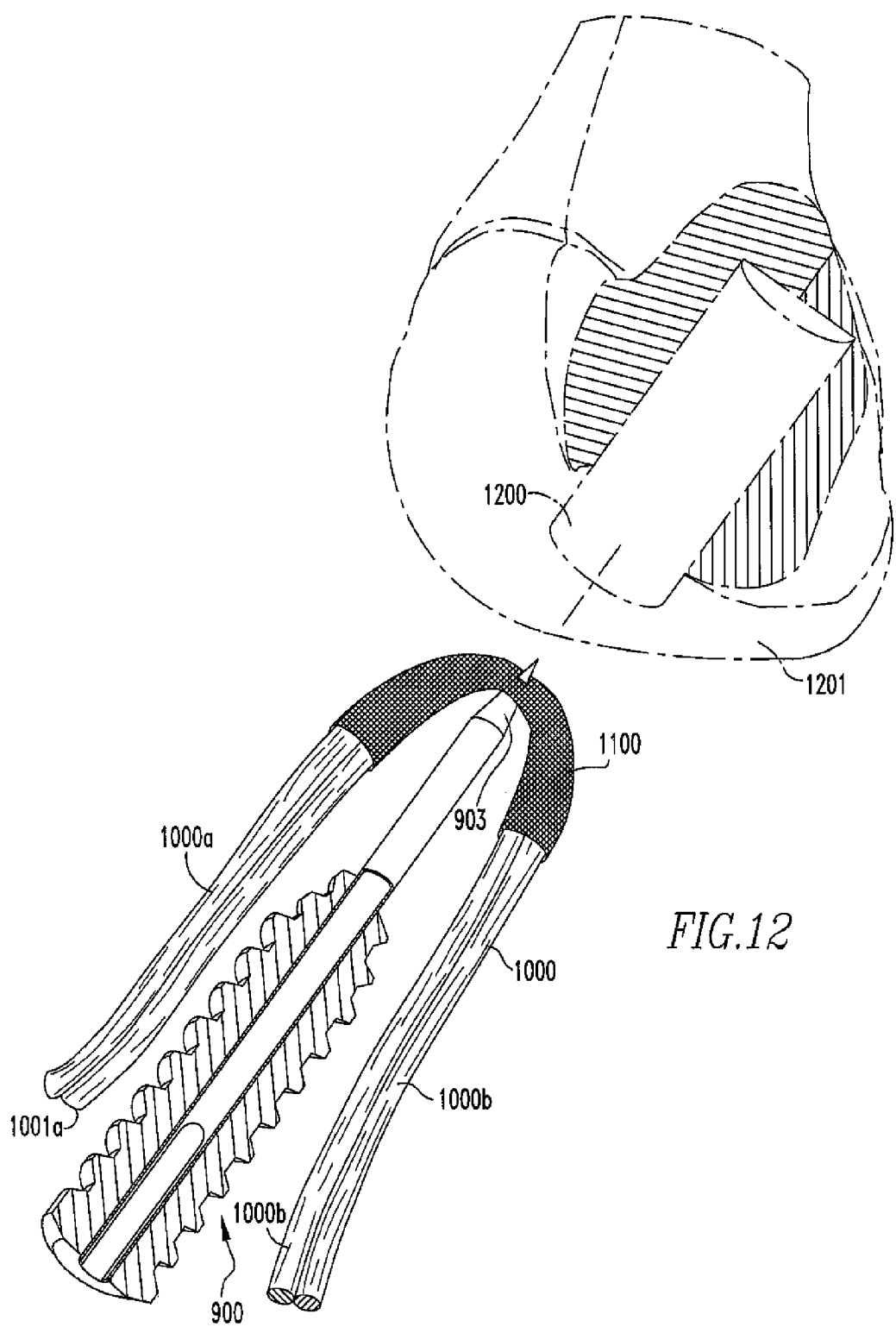
FIG. 12 shows a perspective view of the fourth tissue repair assembly during soft tissue repair wherein the soft tissue strands include a sleeve.

FIGS. 11 and 12 show tissue repair assemblies 900 that are similar to the fourth tissue repair assembly 300 and method shown in FIGS. 7 and 8, albeit including a sleeve of braided or woven material 1100 on the tissue 1000. As shown in FIGS. 11 and 12, one strand or multiple strands of tissue 1000 may be fixated within the tunnel 1200. While the sleeve 1100 is located between the ends 1000a,1000b, it is within the scope of this disclosure for the sleeve 1100 to be located anywhere along the length(s) of the strand(s) 1000 or over the entire strand(s) 1000 prior to placing the tissue(s) 1000 within the bone tunnel 1200. Having the sleeve 1100 on the tissue(s), such as in FIGS. 11 and 12, allows for maintaining the soft tissue(s) 1000 at the tapered end 902 of the interference device 901 via insertion of the fixation device 903 through at least a portion of the sleeve 1100, thereby alleviating the need for the fixation device 903 to be inserted through the soft tissue 1000. However, as shown in FIGS. 11 and 12, it is also within the scope of this disclosure for the fixation device 903 to be inserted through the soft tissue 1000 and the sleeve 1100 or the soft tissue 1000, the sleeve 1100, and the bone 1201. Additionally, rather than using one sleeve 1100 for all of the strands of tissue 1000, as shown in FIG. 12, it is also within the scope of this disclosure to have a sleeve 1100 located on each strand of tissue 1000. A flexible member, such as a suture, may be used to couple the sleeve 1100 to the tissue 1000.

Figure 13A:
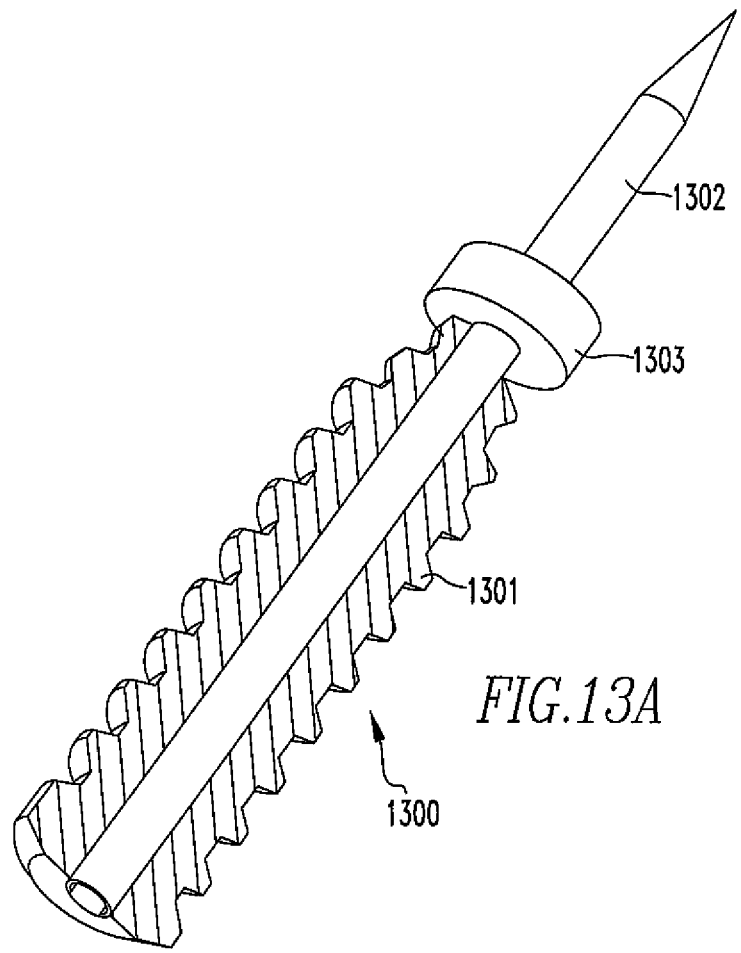
FIG. 13A shows a perspective view of a sixth tissue repair assembly of the present disclosure.

FIG. 13A shows a sixth tissue repair assembly 1300 of the present disclosure that is similar to the fourth tissue repair assembly 300 of FIG. 7. However, assembly 1300 includes a collar 1303 located on the fixation device 1302. When the assembly 1300 is used to fixate soft tissue to bone via a method similar to the method of FIG. 8, the collar 1303 further facilitates maintenance of the location of the soft tissue in front of, or at the tapered end of the interference device 1301.

Figure 13B:
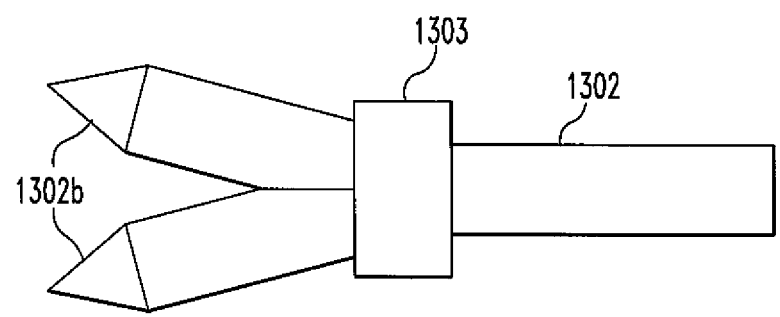
FIG. 13B shows a perspective view of an alternative fixation device for use in the sixth tissue repair assembly of FIG. 13A.

FIG. 13B shows an alternative fixation device 1302 for use with repair assembly 1300. Rather than having one pointed distal end 1302b, the device may have multiple pointed distal ends 1302b. This would allow the device 1300 to capture more of the tissue and therefore provide for increased fixation of the tissue to bone. For the purposes of FIG. 13B, the device 1300 includes only two pointed distal ends 1302b. However, it is within the scope of this disclosure for the device 1300 to include more than two pointed distal ends 1302b.

Figure 14:
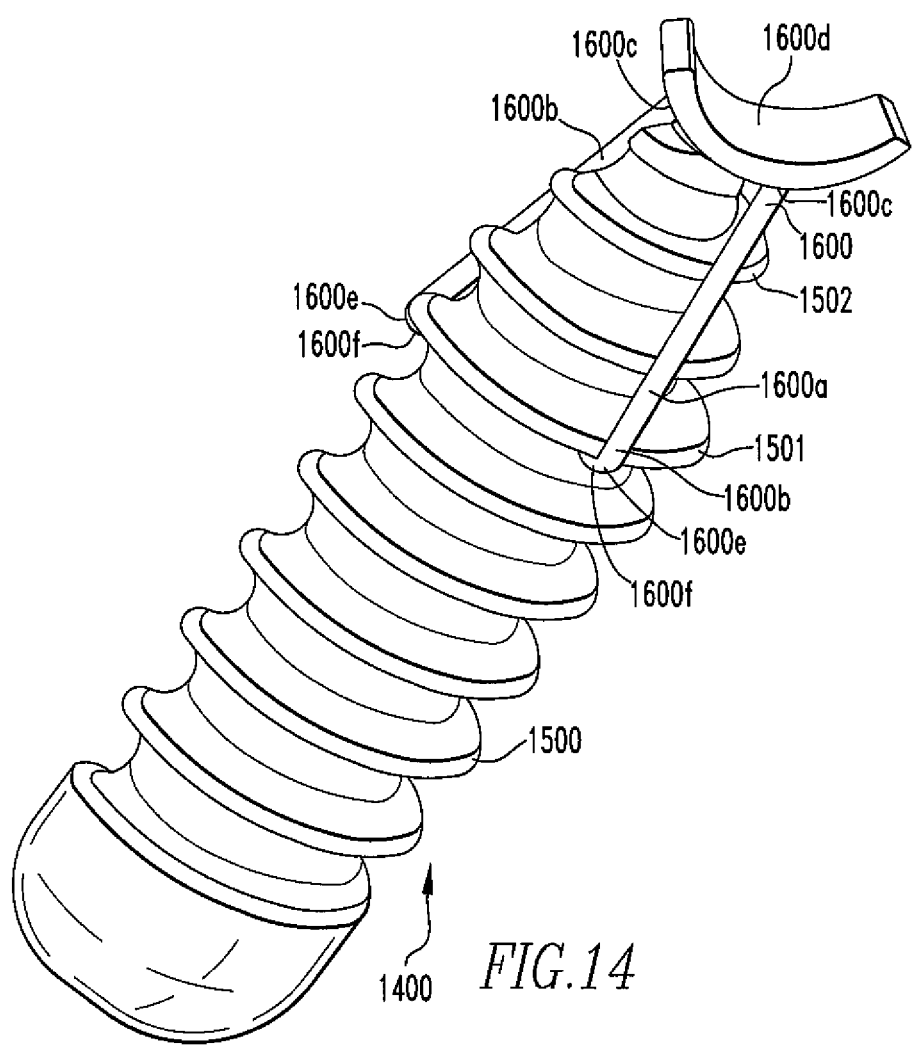
FIG. 14 shows a perspective view of a seventh tissue repair assembly of the present disclosure.

FIG. 14 shows a seventh tissue repair assembly 1400 of the present disclosure that is similar to the tissue repair assembly 10 of FIG. 1. However, instead of shaft 12c, the fixation device 1600 includes a coupling portion 1600a having at least two legs 1600b. Each leg 1600b has one end 1600c coupled to the capturing portion 1600d and another end 1600e coupled to a thread 1501 of the interference device 1500. For the purposes of this disclosure, each end 1600e includes a foot 1600f that allows for snap lock coupling of the foot 1600f to the thread 1501 and therefore coupling of the fixation device 1600 to the interference device 1500. The legs 1600b are tapered to accommodate the tapered end portion 1502 of the device 1500. It is within the scope of this disclosure for the legs 1600b to be of different lengths such that one foot 1600f is coupled to one thread 1501 and the other foot 1600ƒ is coupled to a different thread 1501. It is also within the scope of this disclosure for the coupling portion 1600*a* to have more than two legs 1600*b*. The capturing portion 1600*d* is of a semi-circular shape so as to capture soft tissue in a manner similar to how the capturing portion 12*b* of the assembly 10 of FIGS. 1 and 2 capture tissue. However, the capturing portion 1600*d* may be of any other shape that would allow capturing of the tissue and maintenance of it in front of or at the tapered end 1502 of the interference device 1500 during and after repair. The ends 1600*c*,1600*e* may be coupled to the capturing portion 1600*d* and the interference device 1500 in any manner known to one of skill in the art.

Figure 15:
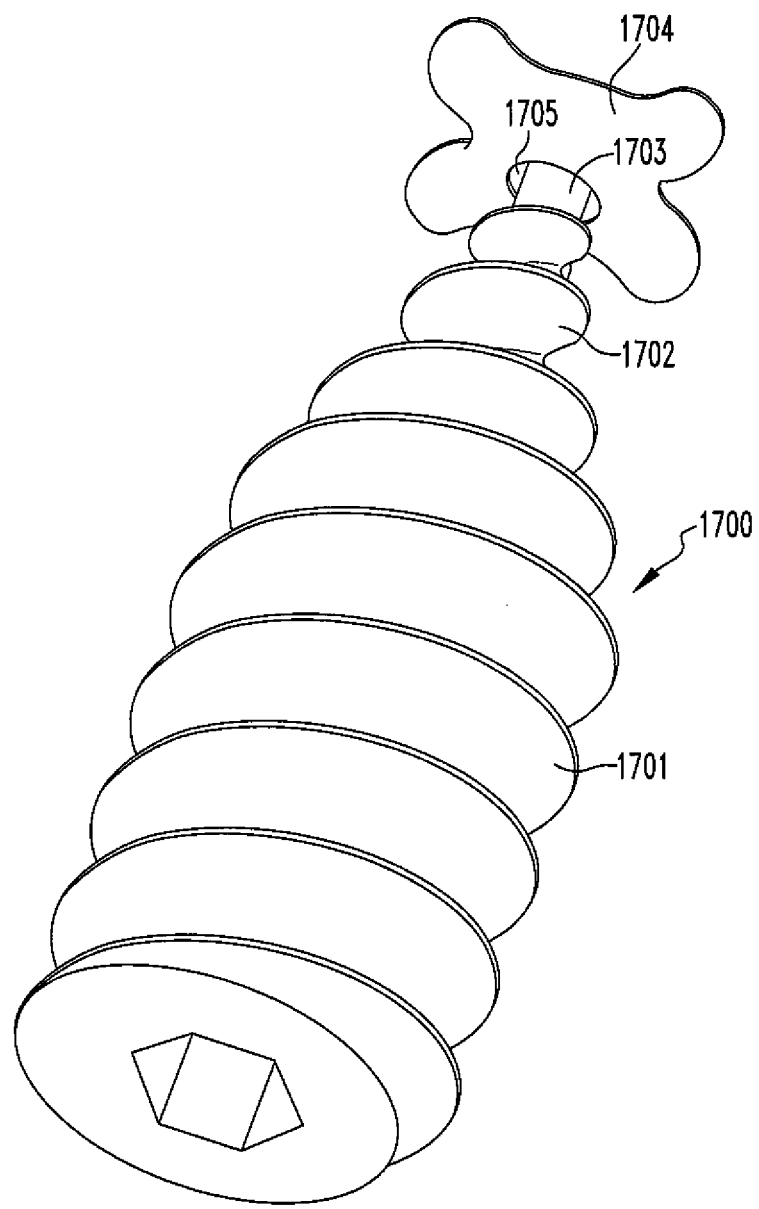
FIG. 15 shows a perspective view of an eighth tissue repair assembly of the present disclosure.

FIG. 15 shows an eighth tissue repair assembly 1700 of the present disclosure. The assembly 1700 is similar to assembly 80 of FIG. 5. However, the interference device 1701 of assembly 1700 includes a tip 1703 that extends beyond the tapered end 1702 of the device 1701. The fixation device 1704 is coupled to the interference device 1701 such that the tip 1703 extends through a center opening 1705 of the device 1704. During repair, soft tissue is disposed on the fixation device 1704 in a manner similar to how soft tissue is disposed on the fixation device 82 of assembly 80 and shown in FIG. 6.

Figure 16:
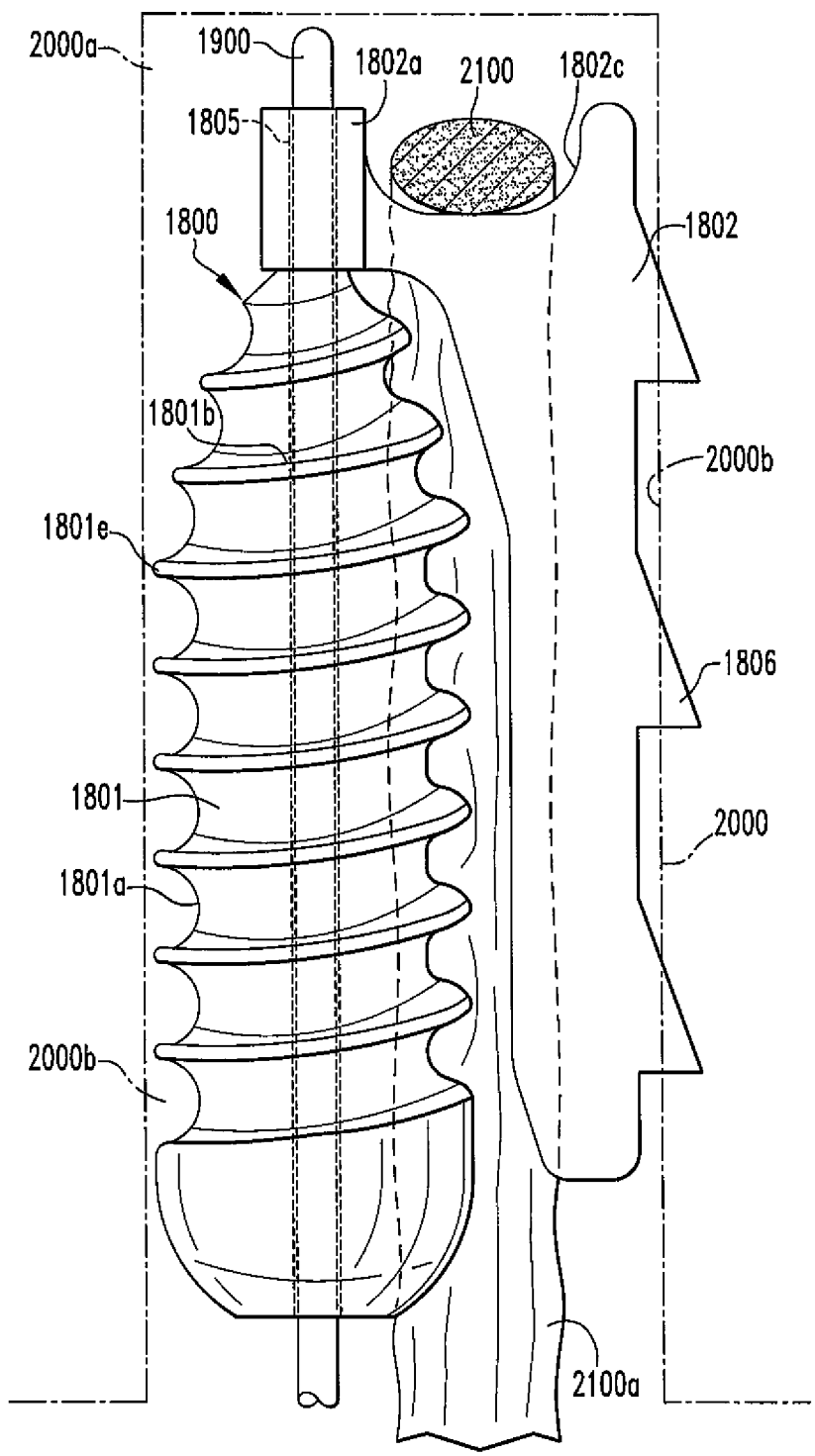
FIG. 16 shows a ninth tissue repair assembly of the present disclosure during soft tissue repair.
Figure 17:
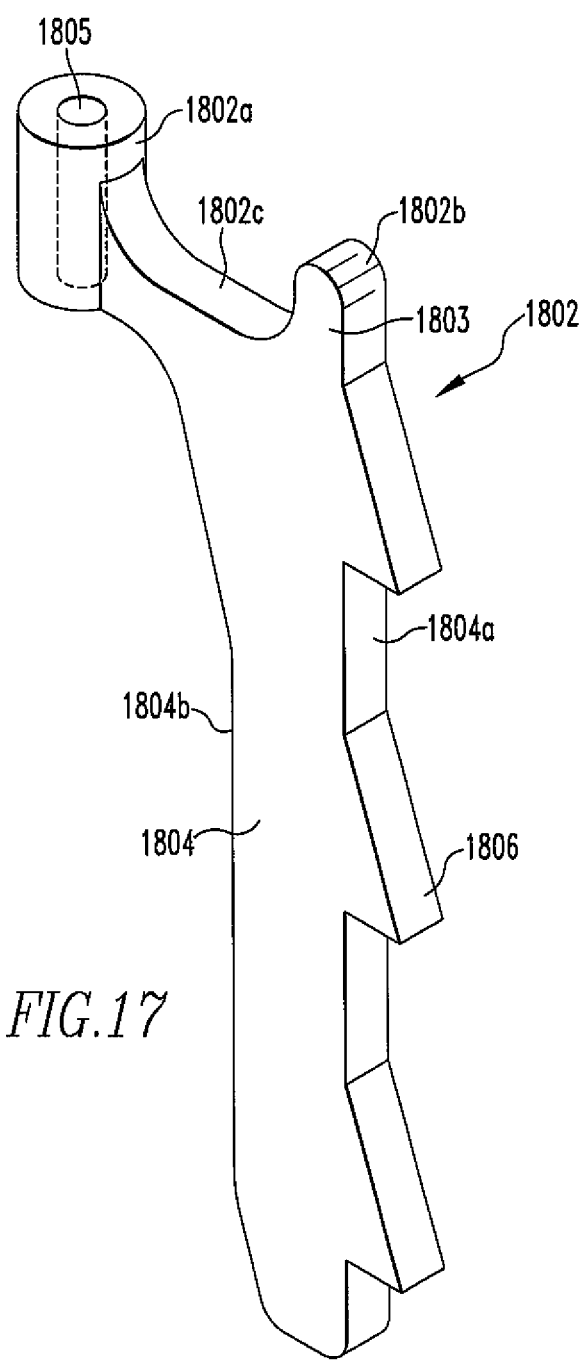
FIG. 17 shows a side view of the fixation device of the tissue repair assembly of FIG. 16.

FIG. 16 shows a ninth tissue repair assembly 1800 of the present disclosure. The assembly 1800 is similar to assembly 600 such that the assembly 1800 includes an interference device 1801 having a tapered body 1801*a* with threads 1801*e* and a cannulation 1801*b* and a fixation device 1802 coupled to the interference device 1801. As shown especially in FIG. 17, the fixation device 1802 includes a first leg 1802*a*, a second leg 1802*b*, and a groove 1802*c* located between the legs 1802*a*,1802*b*. The device 1802 also includes a top portion 1804 extending from the base portion 1803. The first leg 1802*a* includes a through hole 1805 for disposal of a guide wire 1900 during surgery, as shown in FIG. 17 and further described below. The top portion 1804 includes a first side 1804*a* including a plurality of bone engaging elements 1806 and a second side 1804*b*. As will be further described below, the legs 1802*a*,1802*b* and the groove 1802*c* cooperate to house soft tissue within the groove 1802*c* and fixate the tissue within a bone tunnel. For the purposes of FIGS. 16 and 17, the groove 1802*c* is U-shaped. However, the device may be V-shaped or have any other shape known to one of skill in the art. Also for the purposes of this disclosure, plurality means more than one. However, the fixation device 1802 may include a single bone engaging element 1806, rather than a plurality, or it may have no bone engaging elements 1806.

FIG. 16 shows the assembly 1800 located on a guide wire 1900. The guide wire 1900 is advanced into a bone tunnel 2000*a*, such as a tibial tunnel of a knee joint, and the assembly 1800 is disposed on the guide wire 1900, such that the guide wire 1900 is passed through the cannulation 1801*b* and the through hole 1805 of the first leg 1802*a*. A soft tissue graft 2100 is draped over the assembly 1800 such that a portion of the graft 2100 rests in the groove 1802*c* and ends 2100*a*, 2100*b* of the graft 2100 are located between the assembly 1800 and the wall 2000*b* of the bone tunnel 2000*a*. The assembly 1800 and the graft 2100 may be advanced together into the tunnel 2000*a* via a delivery device (not shown) and the guide wire 1900 or in another order or manner known to one of skill in the art. The threads 1801*e* allow for compression of the graft 2100 against the wall 2000*b* of the bone tunnel 2000*a*. Additionally, the interference device 1801 allows for compression of the fixation device 1802 against the wall 2000*b* of the bone tunnel 2000*a*, such that the bone engaging elements 1806 engage the bone 2000, as shown in FIG. 17, thereby facilitating fixation of the graft 2100 within the tunnel 2000*a*.

The top portion 1804 maintains alignment of the fixation device 1802 with respect to the interference device 1801, particularly after removal of the guidewire 1900. As the device 1802 is inserted into the tunnel 2000*a*, tension may be applied to the ends 2100*a*,2100*b* of graft 2100 to maintain parallel alignment with the device 1802 and minimize the possibility of the graft winding around the device 1802. Additionally, the end of the first leg 1802*a* that is in contact with the device 1802 may include a countersink recess to help center the fixation device 1802 with the interference device 1801 when the guidewire 1900 is removed.

As stated above, current fixation of tissue to bone occurs via the use of only an interference device. This method provides fixation based mainly on the friction located between the interference device and the tissue and the friction located between the wall of the bone tunnel and the interference device. Alternatively, the graft fixation that occurs via the use of tissue repair assembly 1800, and other assemblies of the present disclosure, is based mainly on the mechanical locking that occurs between the interference device and the fixation device and the friction that occurs between the threads of the interference device and the wall of the bone tunnel. Due partly to this mechanical locking, the coefficient of friction between the threads and the wall is higher (coefficient of friction >1) when compared to the current method of fixation. This higher coefficient of friction minimizes the possibility of decreased or failed fixation of the tissue to the bone and therefore increases the possibility of a successful repair.

The assemblies 10, 40, 80, 300, 600, 900, 1300, 1400, 1700, 1800 of the present disclosure, and especially the fixation devices 12, 42, 82, 302, 602, 903, 1302, 1600, 1704, 1802 maintain the location of the soft tissue in front of, or at the tapered end of the interference device 11, 41, 81, 301, 601, 901, 1301, 1500, 1701, 1801 thereby preventing slippage of the tissue past the device 11, 41, 81, 301, 601, 901, 1301, 1500, 1701, 1801 during and after repair. This substantially reduces the possibility of a failed fixation of the tissue to the bone, thereby leading to an unsuccessful repair.

For the purposes of this disclosure, the fixation devices and the interference devices are made from a resorbable polymer material. However, a metal material and other non-metal materials, either resorbable or non-resorbable, are also within the scope of this disclosure. In addition, the devices may be made via a molding process or other process known to one of skill in the art. The cannulations and channel may be formed during the molding process or after the molding process by drilling. Furthermore, rather than containing threads, the outer surface of the interference device may include other surface features that would allow engagement of the interference device with the bone tunnel and soft tissue. The threads allow for rotary advancement of the assembly and the soft tissue graft into the tunnel. However, these other surface features may allow for other advancement, such as axial advancement, into the tunnel. Also, the number of surface features may vary.

In addition, the fixation devices may be coupled to the interference devices in manners other than those described above. For the purposes of this disclosure, the method and devices, described above, are used in arthroscopic knee repair. However, the method and devices may be used in the repair of other soft tissue. The fixation devices may be of a variety of lengths and may include surface features that mate with surface features located within the cannulations to further couple the fixation devices to the interference devices.

The surface features may include threads, barbs, ribs, or other surface features known to one of skill in the art and that have the ability to further facilitate coupling between the fixation devices and the interference devices. It is also within the scope of this disclosure for the fixation devices and/or the interference devices to be made out of a material, such as a shape memory material, that expands or otherwise allows for further coupling between the devices in response to body temperature or an external energy source.

Furthermore, it is within the scope of FIGS. 1, 3, and 14 for the fixation devices 12,42,1600 to be coupled to the interference devices 11,41,1500 via the use of a hole on the fixation devices 12,42,1600 that at least the tapered ends 11*d*,41*d*, 1502 are disposed within, rather than using the shafts 12*c*, 42*c*, couplers 12*d*,42*d*, and legs 1600*b*. Additionally, it is within the scope of FIGS. 1, 3, 5, and 14 for the fixation devices 12, 42, 82, 1600 to be coupled to the interference devices 11, 41, 81, 1500 via the use of a shaft that would extend from the coupling portions 12*a*, 42*a*, 82*a*, 1600*a* to be housed within the cannulations 11*b*, 41*b*, 81*b* of the interference devices 11, 41, 81, 1500.

Additionally, it is within the scope of this disclosure for the top portion 604 of fixation device 602 and fixation devices 903,1302 to have a length that extends either an entire length or a partial length of the interference devices 301,601,901, 1301.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A fixation device comprising:
   a base portion including a first leg, a second leg, and a groove located between the first and second legs;
   a top portion extending from the base portion; and
   a threaded interference device including a cannulation, the cannulation including a uniform diameter, the threads located on an outer surface of the interference device.

2. The fixation device of claim 1 wherein the groove is U-shaped.

3. A tissue repair assembly comprising:
   a fixation device comprising a base portion including a first leg, a second leg, and a groove located between the first and second legs, and a cylindrical top portion extending from the base portion; and
   an interference device coupled to the fixation device, the interference device including a cannulation along its length, the cannulation including a uniform diameter.

4. The tissue repair assembly of claim 3 wherein the interference device includes threads on an outer surface of the interference device.

5. The tissue repair assembly of claim 3 wherein the interference device is configured for rotary advancement into a target tissue.

6. A method of tissue repair comprising:
   preparing a hole in a bone; and
   fixating a soft tissue into the hole via the use of a tissue repair assembly comprising a fixation device comprising a base portion including a first leg, a second leg, and a groove located between the first and second legs, and a cylindrical top portion extending from the base portion; and an interference device coupled to the fixation device, wherein the soft tissue is located within the groove of the fixation device when the soft tissue is fixated within the hole and the interference device includes threads on an outer surface of the interference device and a cannulation along its length, the cannulation including a uniform diameter.

7. The method of claim 6 wherein the step of fixating a soft tissue into the hole further comprises inserting the soft tissue into the hole and inserting the tissue repair assembly into the hole to fixate the soft tissue within the hole.

8. The method of claim 6 wherein the step of fixating a soft tissue into the hole further comprises inserting the soft tissue and the tissue repair assembly into the hole together.

9. The method of claim 6 wherein the threads allow for compression of the graft against the bone.

\* \* \* \* \*